United States Patent
Okabe et al.

(10) Patent No.: US 12,410,287 B2
(45) Date of Patent: Sep. 9, 2025

(54) COMPOSITE RESIN MOLDED PRODUCT WITH ADJUSTED DECOMPOSITION RATE, AND PRODUCTION METHOD THEREFOR

(71) Applicant: Panasonic Intellectual Property Management Co., Ltd., Osaka (JP)

(72) Inventors: Ami Okabe, Osaka (JP); Toshifumi Nagino, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 453 days.

(21) Appl. No.: 17/659,783

(22) Filed: Apr. 19, 2022

(65) Prior Publication Data

US 2022/0348727 A1    Nov. 3, 2022

(30) Foreign Application Priority Data

Apr. 30, 2021    (JP) .................... 2021-077721

(51) Int. Cl.
   *C08J 5/04*    (2006.01)
   *C08J 3/22*    (2006.01)
   (Continued)

(52) U.S. Cl.
   CPC ............... *C08J 5/045* (2013.01); *C08J 3/226* (2013.01); *C08J 7/0427* (2020.01); *C12N 11/02* (2013.01); *C12N 11/04* (2013.01); *C08J 2300/16* (2013.01)

(58) Field of Classification Search
   CPC ....... C08J 5/045; C08J 5/18; C08J 5/06; C08J 2497/02; C08J 2401/02; C08J 2300/16;
   (Continued)

(56) References Cited

U.S. PATENT DOCUMENTS

2020/0164332 A1    5/2020    Demoulin et al.

FOREIGN PATENT DOCUMENTS

| JP | 2002-356623 | 12/2002 |
|----|-------------|---------|
| JP | 2013-209587 | 10/2013 |

(Continued)

OTHER PUBLICATIONS

Pommet et al., Surface modification of natural fibers using bacteria: depositing bacterial cellulose onto natural fibers to create hierarchical fiber reinforced nanocomposites, Biomacromolecules Jun. 6, 2008.*

*Primary Examiner* — Camie S Thompson
(74) *Attorney, Agent, or Firm* — WENDEROTH, LIND & PONACK, L.L.P.

(57) ABSTRACT

A composite resin molded product of the invention is a composite resin molded product, including: a main agent resin; and a plurality of natural fibers dispersed in the main agent resin. The plurality of natural fibers each contain a microorganism or an enzyme. When the composite resin molded product is 100% by mass, a content rate of the plurality of natural fibers each containing the microorganism or the enzyme in the composite resin molded product is 10% by mass or more and 99% by mass or less. At least one of the plurality of natural fibers is exposed on a surface of the composite resin molded product. At least a part of a surface of the at least one of the plurality of natural fibers is coated with a hydrolyzable coating resin.

12 Claims, 3 Drawing Sheets

(51) Int. Cl.
*C08J 7/04* (2020.01)
*C12N 11/02* (2006.01)
*C12N 11/04* (2006.01)

(58) Field of Classification Search
CPC ....... C08J 2367/04; C08J 3/226; C08L 67/04;
C12N 11/12; C12N 11/04; C12N 11/02;
C08K 7/02
USPC .......................................................... 428/375
See application file for complete search history.

(56) References Cited

FOREIGN PATENT DOCUMENTS

| | | |
|---|---|---|
| JP | 2019-034987 | 3/2019 |
| JP | 2020-520794 | 7/2020 |
| JP | 2021-021041 | 2/2021 |
| WO | 2020/138496 | 7/2020 |
| WO | 2021/040046 | 3/2021 |

\* cited by examiner

FIG. 5

| | Main agent resin | Fiber | Coating resin | Method for including enzyme | Moisture percentage of fiber [%] | End parts defibrated | Elastic modulus [MPa] | Elastic modulus Evaluation | Decrease rate of elastic modulus [%] | Decrease rate of elastic modulus Evaluation | Biodegradation rate [%] | Biodegradation rate Evaluation |
|---|---|---|---|---|---|---|---|---|---|---|---|---|
| Example 1 | PHBV | Cellulose | Polylactic acid | Supporting | 6.5 | Yes | 259 | B | 5 | B | 42 | B |
| Example 2 | PHBV | Cellulose | Polylactic acid | Supporting | 6.5 | Yes | 242 | B | 4 | B | 54 | A |
| Comparative example 1 | PHBV | Cellulose | - | Supporting | 6.5 | Yes | 236 | B | 3 | B | 25 | C |
| Comparative example 2 | PHBV | - | Polylactic acid | Kneading | - | - | 220 | B | 12 | C | 27 | C |
| Comparative example 3 | PHBV | PET fiber | Polylactic acid | Supporting | 0.4 | No | 255 | B | 4 | B | 20 | C |
| Comparative example 4 | Polylactic acid | Cellulose | Polylactic acid | Supporting | 6.5 | Yes | 270 | B | 25 | C | 11 | C |
| Comparative example 5 | PHBV | - | - | - | - | - | 193 | C | 1 | B | 28 | C |

COMPOSITE RESIN MOLDED PRODUCT WITH ADJUSTED DECOMPOSITION RATE, AND PRODUCTION METHOD THEREFOR

BACKGROUND

1. Technical Field

The present invention relates to a composite resin molded product with satisfactory mechanical characteristics and adjusted biodegradation speed in humid environments, and a production method therefor.

2. Description of the Related Art

So-called "general-purpose plastics", such as polyethylene (PE), polypropylene (PP), polystyrene (PS), polyvinyl chloride (PVC), and the like are rather inexpensive, easy to mold, and have a weight several times lighter than metals or ceramics. Thus, the general-purpose plastics are often used as materials for various daily necessities such as bags, various packaging, various containers, and sheets, or materials for industrial parts such as automobile parts and electric parts, as well as necessaries for daily use and miscellaneous goods.

Under such circumstances, amounts of plastic wastes after use, which are substances difficult to decompose, increase year by year, resulting in accumulations of the plastic wastes in the natural environment. Consequently, the accumulations cause pollution problems such as destruction and pollution of the natural environment. In recent years, as one of the measures to solve such problems, biodegradable plastics that decompose into water and carbon dioxide in the natural environment have been proposed, and are expected to be expandingly used in place of the general-purpose plastics, which are made from petroleum-based raw materials.

The biodegradable plastics, however, have drawbacks such as insufficient mechanical strength as compared with the general-purpose plastics. Consequently, the biodegradable plastics do not have sufficient characteristics required for materials used in mechanical products such as automobiles and various industrial products such as electrical, electronic and informational products, and thus are currently limited in the scope of application. Moreover, many biodegradable plastics are easily decomposed due to the characteristics thereof, and have a problem that hydrolysis proceeds during use and the rigidity is deteriorated.

On the other hand, the biodegradation speed of the biodegradable plastics after disposal is greatly affected by the environment. In an environment with few microorganisms, such as in the ocean, complete decomposition takes a significant amount of time, and the biodegradability property is not fully utilized. In order to solve such a problem, various methods for accelerating the decomposition of the biodegradable plastics after disposal have been proposed.

For example, a method of applying or blending a biodegradable plastic containing a microorganism having an enzymatic activity that decomposes the biodegradable plastic (see, for example, Japanese Patent Unexamined Publication No. 2013-209587), and a method of pre-microencapsulating a microorganism and incorporating the microorganism into a biodegradable plastic (see, for example, Japanese Patent Unexamined Publication No. 2020-520794) have been disclosed.

SUMMARY

A composite resin molded product according to one aspect of the invention is a composite resin molded product including: a main agent resin; and a plurality of natural fibers dispersed in the main agent resin. The plurality of natural fibers each contain a microorganism or an enzyme. When the composite resin molded product is 100% by mass, a content rate of the plurality of natural fibers each containing the microorganism or the enzyme in the composite resin molded product is 10% by mass or more and 99% by mass or less. At least one of the plurality of natural fibers is exposed on a surface of the composite resin molded product. At least a part of a surface of the at least one of the plurality of natural fibers is coated with a hydrolyzable coating resin.

A production method for a composite resin molded product according to one aspect of the invention includes: a step of preparing an microorganism or an enzyme, natural fibers, a hydrolyzable coating resin, and a main agent resin; a step of including the microorganism or enzyme in the natural fibers; a coating resin melt-kneading step of melt-kneading the natural fibers containing the microorganism or enzyme together with the coating resin, advancing defibration from an end part in a fiber length direction of each of the natural fibers containing the microorganism or enzyme, and expanding a surface area of a defibrated part of the end part; and a step of molding the composite resin molded product after kneading coated natural fibers, obtained by coating at least a part of a surface of each of the natural fibers with the coating resin, together with the main agent resin.

BRIEF DESCRIPTION OF THE DRAWINGS

FIG. 5 is a diagram illustrating configurations and measurement results of composite resin molded products in examples and comparative examples in the embodiments.

DESCRIPTION OF THE PREFERRED EMBODIMENTS

Figure 1:
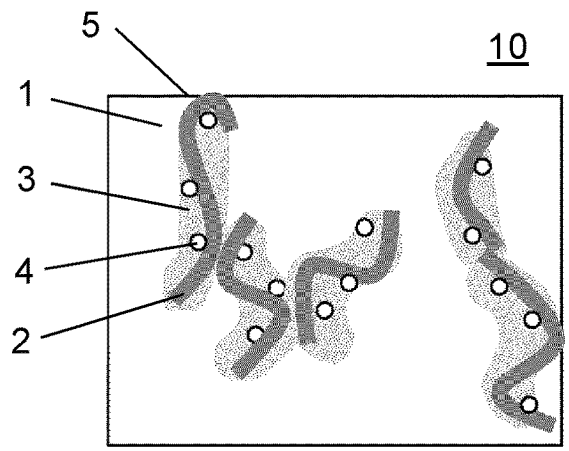
FIG. 1 is a schematic cross-sectional view illustrating a cross-sectional structure of a composite resin molded product according to Embodiment 1.

In the method described in Japanese Patent Unexamined Publication No. 2013-209587, since the microorganism is directly kneaded into the biodegradable plastic, the material is limited to biodegradable plastics that can be molded at a temperature at which the microorganism can survive. On the other hand, in the method described in Japanese Patent Unexamined Publication No. 2020-520794, in order to release the microorganism from a microcapsule, it is necessary to physically damage the molded product, and the rigidity of the molded product decreases as the content of the microcapsule increases.

The invention solves the above-described problems of the related art, and has a purpose of providing a composite resin molded product that maintains high rigidity during use and promotes biodegradation after disposal in humid environments such as in the ocean or soil.

A composite resin molded product according to a first aspect is a composite resin molded product including: a main agent resin; and a plurality of natural fibers dispersed in the main agent resin. The plurality of natural fibers each contain a microorganism or an enzyme. When the composite resin molded product is 100% by mass, a content rate of the plurality of natural fibers each containing the microorganism or the enzyme in the composite resin molded product is 10% by mass or more and 99% by mass or less. At least one of the plurality of natural fibers is exposed on a surface of the composite resin molded product. At least a part of a surface of the at least one of the plurality of natural fibers is coated with a hydrolyzable coating resin.

Regarding a composite resin molded product according to a second aspect, in the first aspect, a moisture percentage in the plurality of natural fibers may be 5% or more by a method specified in ASTM D 1909.

Regarding a composite resin molded product according to a third aspect, in the first or second aspect, the main agent resin in the composite resin molded product may be a biodegradable resin containing any one selected from the group of polyhydroxyic acids, polyhydroxyalkanoates, poly(alkylene dicarboxylate)s, and modified starches.

Regarding a composite resin molded product according to a fourth aspect, in any of the first to third aspects, the hydrolysable coating resin may have a melting point within a range equal to or higher than a melting point of the main agent resin and lower than a carbonization temperature of the plurality of natural fibers.

Regarding a composite resin molded product according to a fifth aspect, in any of the first to fourth aspects, the plurality of natural fibers may each contain a fiber and the microorganism or enzyme supported on a surface of the fiber.

Regarding a composite resin molded product according to a sixth aspect, in any of the first to fifth aspects, the plurality of natural fibers may be celluloses.

Regarding a composite resin molded product according to a seventh aspect, in any of the first to sixth aspects, at least one of the plurality of natural fibers may include a defibrated part at an end part in a fiber length direction.

A production method for a composite resin molded product according to an eighth aspect includes: a step of preparing a microorganism or an enzyme, natural fibers, a hydrolyzable coating resin, and a main agent resin; a step of including the microorganism or enzyme in the natural fibers; a coating resin melt-kneading step of melt-kneading the natural fibers containing the microorganism or enzyme together with the coating resin, advancing defibration from an end part in a fiber length direction of each of the natural fibers containing the microorganism or enzyme, and expanding a surface area of a defibrated part of the end part; and a step of molding the composite resin molded product after kneading coated natural fibers, obtained by coating at least a part of a surface of each of the natural fibers with the coating resin, together with the main agent resin.

Regarding a production method for a composite resin molded product according to a ninth aspect, in the eighth aspect, a molding temperature in the step of molding the composite resin molded product may be set to a temperature of 125% or less of a melting point of the coating resin.

According to the composite resin molded product according to one aspect of the invention, it is possible to implement a composite resin molded product that has a biodegradation speed controlled in humid environments in addition to a higher elastic modulus as compared to a resin alone.

Hereinafter, a composite resin molded product and a production method therefor according to the embodiment will be described with reference to the attached drawings. In the following description, the same components are designated by the same reference numerals, and the descriptions thereof are omitted as appropriate.

Embodiment 1

Figure 2:
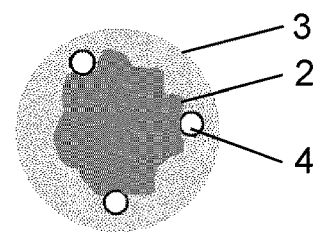
FIG. 2 is a schematic cross-sectional view illustrating a cross-sectional structure of a natural fiber which is a component of the composite resin molded product according to Embodiment 1.

FIG. 1 is a schematic cross-sectional view illustrating a cross-sectional structure of composite resin molded product 10 according to Embodiment 1. FIG. 2 is a schematic cross-sectional view illustrating a cross-sectional structure of a natural fiber which is a component of composite resin molded product 10 according to Embodiment 1.

Composite resin molded product 10 according to Embodiment 1 is made of a melt-kneaded product of main agent resin 1 and natural fibers 2 each containing microorganism or enzyme 4 coated with coating resin 3. In composite resin molded product 10, as illustrated in the schematic cross-sectional view of FIG. 1, natural fibers 2 containing microorganism or enzyme 4 coated with coating resin 3 are dispersed in main agent resin 1.

Since at least one of natural fibers 2 is exposed on surface 5 of composite resin molded product 10 and natural fibers 2 have contact points with each other, composite resin molded product 10 has a high elastic modulus and high water absorption. When coating resin 3 is hydrolyzed by the water absorption of natural fibers 2 in humid environments, microorganism or enzyme 4 supported on natural fibers 2 is released, thereby promoting the decomposition of main agent resin 1. Thus, it is possible to implement composite resin molded product 10 that maintains high rigidity during use and has satisfactory biodegradability after disposal in humid environments such as in the ocean or soil.

Hereinafter, each member constituting the composite resin molded product will be described.

<Main Agent Resin>

In the present embodiment, main agent resin 1 is preferably a biodegradable plastic containing any one selected from the group of polyhydroxy acids, polyhydroxyalkanoates, poly(alkylene dicarboxylate)s, and modified starches. In order to ensure satisfactory moldability, a thermoplastic resin is preferable, and the above-described resins may be used alone or in combination of two or more. Main agent resin 1 is not limited to the above-described materials as long as the resin has biodegradability.

In the present embodiment, the "biodegradable plastics" refers to "resins having the same function as a petroleum-derived resin in the related art when used, and finally decomposed into water and carbon dioxide by microorganisms in natural soil or ocean after use". Specifical examples thereof include: polyester resins, such as polyhydroxyalkanoates including polyhydroxybutyrate and polyhydroxyvalirate, polyhydroxy acids including polylactic acid, polyglycolic acid, and polycaprolactone, and polyalkylene dicarboxylates including polybutylene adipate terephthalate, polyethylene succinate, and polybutylene succinate; and modified starches. The polyester resins include, in addition to homopolymers of polyester-based monomer, copolymers of polyester-based monomers such as poly(3-hydroxybutyrate-co-3-hydroxyvariate), and copolymers of polyester-based monomers and other copolymerizable monomers. These polyester resins may be used alone or in combination of two or more.

<Natural Fiber>

Next, natural fibers 2 will be described. The first main purpose of adding natural fibers 2 (hereinafter, may be simply referred to as "the fiber") contained in composite resin molded product 10 in the present embodiment is to bring into contact with water and hydrolyze coating resin 3 by absorbing water in the soil or the ocean without giving a load to the environment when composite resin molded product 10 is disposed after use. For this purpose, natural fibers 2 preferably have high water absorption, and the moisture percentage of natural fibers 2 is preferably 5% or more by the method specified in ASTM D 1909. Specifically, pulp, cellulose, cellulose nanofibers, lignocellulose, lignocellulose nanofibers, cotton, silk, linen or the like are preferable.

The second purpose of adding natural fibers 2 is to improve the mechanical characteristics and the dimensional stability by lowering the linear expansion coefficient. For this purpose, natural fibers 2 preferably have a higher elastic modulus than that of main agent resin 1. Specifical examples thereof include pulp, cellulose, cellulose nanofibers, lignocellulose, lignocellulose nanofibers, cotton, silk, wool, linen, or the like. Among these materials, celluloses are particularly preferable from the viewpoints of availability, high elastic modulus, and low linear expansion coefficient. Natural fibers 2 are not limited to the above-described materials as long as the material can improve mechanical characteristics and has water absorption.

After microorganism or enzyme 4 is included in natural fibers 2, when composite resin molded product 10 is 100% by mass, the content rate of natural fibers 2 containing microorganism or enzyme 4 in composite resin molded product 10 is preferably 10% by mass or more and 99% by mass or less. When the content rate of natural fibers 2 containing microorganism or enzyme 4 is less than 10% by mass, natural fibers 2 cannot easily have the contact points with each other inside composite resin molded product 10 and cannot have sufficient water absorption. On the other hand, when the content rate of natural fibers 2 containing microorganism or enzyme 4 is larger than 99% by mass, the proportion of main agent resin 1 and coating resin 3 is small, and thus the effect of adhering natural fibers 2 to each other is lost and the moldability is deteriorated.

Figure 3:
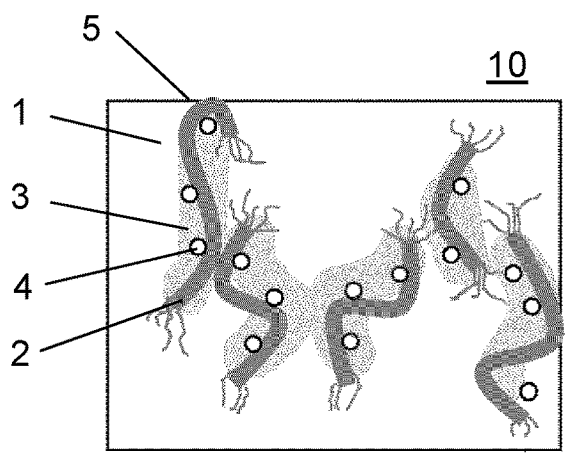
FIG. 3 is a schematic cross-sectional view illustrating a cross-sectional structure of the composite resin molded product containing natural fibers each having a defibrated part according to Embodiment 1.

The form of natural fibers 2 in composite resin molded product 10 will be described. It is preferable that a larger bonding interface between natural fibers 2 and coating resin 3 results in a higher specific surface area of natural fibers 2, because the hydrolysis of coating resin 3 is promoted when natural fibers 2 absorb water. On the other hand, in order to improve the water absorption of composite resin molded product 10, natural fibers 2 are preferably exposed on the surface of composite resin molded product 10. Since natural fibers 2 are exposed on the surface of composite resin molded product 10, natural fibers 2 absorb water from the exposed part and absorbs water to the inside of composite resin molded product 10 by the capillary phenomenon of the fibers constituting the natural fibers. Natural fibers 2 exposed on the surface of the composite resin molded product have a higher water absorption as the specific surface area is smaller. This is because when the specific surface area of natural fibers 2 exposed on the surface is large, the water repellency is enhanced by the effect of fine irregularities. As illustrated in FIG. 3, a defibrated part at an end part of each of natural fibers 2 increases the specific surface area of the defibrated part and increases contact points between natural fibers 2, thereby allowing to increase the water absorption rate through the contact points of natural fibers 2 in the humid environments.

An undefibrated central part of each of natural fiber 2, which has a small specific surface area, is less entangled with main agent resin 1 and is easily exposed on the surface of the composite resin molded product depending on molding conditions. On the contrary, a tip part of each of defibrated natural fiber 2 is often entangled with main agent resin 1 and enters the inside together with main agent resin 1. As a result, it is possible to obtain composite resin molded product 10 in which the central part of natural fiber 2 without including both the end parts are exposed on the surface.

The defibrated part on the tip is preferably 5% or more and 50% or less of fiber length L of entire natural fiber 2. When the defibrated part is less than 5% of total fiber length L, the elastic modulus is not improved because the specific surface area is small, and when the defibrated part is longer than 50%, the defibrated part, which has a large aspect ratio, is exposed on the surface of the composite resin molded product, and the water absorption is deteriorated.

Next, the characteristics of natural fibers 2 will be described. The types of main agent resin 1 and natural fibers 2 are as described above, but when natural fibers 2 are too soft with respect to main agent resin 1, that is, when the elastic modulus is small, the elastic modulus of composite resin molded product 10 as a whole becomes small, which as a result decreases the strength. On the other hand, when natural fibers 2 are too hard with respect to main agent resin 1, that is, when the elastic modulus is large, a shock wave generated at the time of impact is not propagated but is absorbed at the interface between main agent resin 1 and natural fibers 2. Therefore, cracks and crazes are likely to occur near the interface, and as a result, the impact resistance is lowered. Consequently, regarding the relation of the elastic modulus between main agent resin 1 and natural fibers 2, it is preferable that the elastic modulus of natural fibers 2 is higher and the difference therebetween is as small as possible. The optimum relation is calculated from a simulation result, and the elastic modulus difference between main agent resin 1 and natural fibers 2 is preferably within 20 GPa.

These natural fibers 2 may be surface-treated for the purpose of improving the adhesiveness with main agent resin 1 and coating resin 3 or the dispersibility in composite resin molded product 10, but when the surface treatment impairs the water absorption of natural fibers 2, it is preferable not to perform the surface treatment in advance.

<Additives>

Additives may be used as necessary for the purpose of improving the affinity between main agent resin 1 and natural fibers 2. Any normally used additives can be used.

<Coating Resin>

Next, coating resin 3 will be described. Coating resin 3 in the present embodiment is used for the purpose of protecting microorganism or enzyme 4 supported on natural fibers 2 and preventing the contact with main agent resin 1 during the use of composite resin molded product 10. After disposal of composite resin molded product 10, in order to promote the biodegradation in the humid environments, coating resin 3 needs to be decomposed to release microorganism or enzyme 4 supported on natural fibers 2. Therefore, coating resin 3 is preferably a hydrolyzable resin that decomposes in an environment having a humidity of 50% or more. Specific examples thereof include polyester resins such as polylactic acid, polybutylene terephthalate, and polycarbonate. In order to ensure satisfactory moldability, a thermoplastic resin is preferable, and the above-described resins may be used alone or in combination of two or more. Coating resin 3 is not limited to the above-described materials as long as the material has hydrolysis characteristics.

Coating resin 3 maintains a state of being coated on at least a part of the surface of natural fibers 2 in composite resin molded product 10, and thus, it is preferable that coating resin 3 has a melting point within a range of equal to or higher than a melting point of main agent resin 1 and lower than a carbonization temperature of natural fibers 2. When the melting point of coating resin 3 is equal to or higher than the melting point of main agent resin 1, composite resin molded product 10 does not melt during molding, and when the temperature is lower than the carbonization temperature of natural fibers 2, natural fibers 2 can be coated without deterioration.

The existence state of coating resin 3 in composite resin molded product 10 will be described. By controlling the coated rate of natural fibers 2, coating resin 3 can delay the release of microorganism or enzyme 4 supported on natural fibers 2 and control the decomposition rate.

<Microorganism or Enzyme>

Next, microorganism or enzyme 4 will be described. Microorganism or enzyme 4 in the present embodiment are used for the purpose of accelerating the decomposition of composite resin molded product 10 in the humid environments. Microorganism or enzyme 4 in the present embodiment varies according to main agent resin 1, and specific examples thereof include *Amycolatopsis* microorganisms as polylactic acid degradants and polybutylene succinate degradants; *Streptomyces* microorganisms, *Pseudomonas* microorganisms such as *Pseudomonas lemoignei*, and *Alcaligenes* microorganisms such as *Alcaligenes paradoxus* as poly(3-hydroxybutyric acid) degradants; and *Pseudomonas* microorganisms such as *Pseudomonas stutzeri*, *Pseudomonas aeruginosa*, *Pseudomonas vesicularis*, *Alcaligenes* microorganisms, *Acinetobacter* microorganisms, and *Xanthomonas* microorganisms as degradants of polyether such as polyethylene glycol.

The enzyme in the present embodiment may be various enzymes extracted from, for example, the above-described microorganisms. Specific examples thereof include: Proteinase K as an enzyme for decomposing polylactic acid; polyvinyl alcohol dehydrogenase, polyvinyl alcohol oxidase, secondary alcohol oxidase and the like for decomposing polyvinyl alcohol; PHB depolymerase as an enzyme for decomposing poly3-hydroxybutyric acid; and cholesterol esterase, Chitopearl cholesterol esterase, urease and the like as enzymes for decomposing polyurethane. The above-described microorganism or enzyme may be used alone or in combination of two or more. The material is not limited to the above-described materials as long as the material has degradability with respect to main agent resin 1.

<Production Method for Composite Resin Molded Product>

Figure 4:
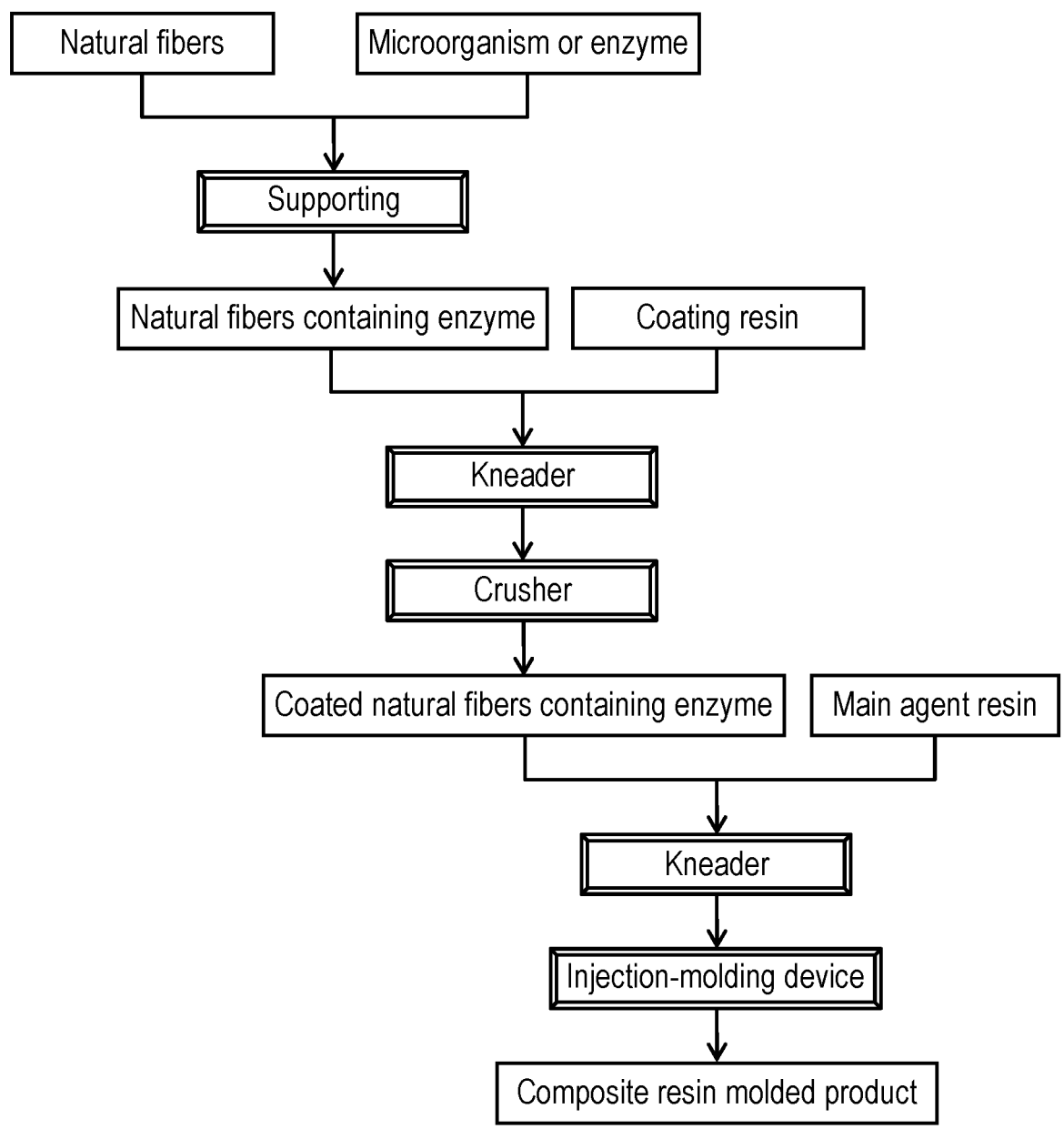
FIG. 4 is a schematic diagram of a producing process of the composite resin molded product according to Embodiment 1.

Next, a production method for composite resin molded product 10 will be described. FIG. 4 is a flow chart exemplifying a producing process of composite resin molded product 10 in the present embodiment.

(1) Microorganism or enzyme 4 is supported on the surface of natural fibers 2 in advance. Methods for supporting microorganism or enzyme 4 include physical adsorption by dry blending, impregnation method of natural fibers using a dispersion solvent, cross-linking method, comprehensive method and the like. The method for supporting the microorganism or enzyme is not limited to the above-described methods as long as the method can retain microorganism or enzyme 4 on the surface of natural fibers 2.

(2) Natural fibers 2 and coating resin 3 are put into a melt-kneading device and are melt-kneaded in the device. As a result, coating resin 3 is melted, and natural fibers 2 are dispersed in the melted coating resin 3. At the same time, the shearing action of the device promotes the defibration of agglomerates of natural fibers 2, and natural fibers 2 can be finely dispersed in coating resin 3. In this case, by adjusting the shearing conditions, as illustrated in FIG. 3, the end parts of natural fibers 2 can be defibrated to obtain the defibrated parts.

In order to compound fibers with a resin, the related art uses fibers that are defibrated in advance by a pretreatment such as wet dispersion. Nevertheless, when the natural fibers are defibrated in a solvent used for wet dispersion, the fibers swell due to the solvent, and thus, in order for the natural fibers to sufficiently absorb water and expand in the composite resin molded product, it is necessary to dry the solvent in the natural fibers before kneading the natural fibers with the main agent resin. Moreover, the fibers are more easily defibrated by the wet dispersion than in the molten main agent resin, and the end parts are difficult to defibrate alone, which causes a state that the entire natural fibers are defibrated. Due to the addition of the pretreatment, there is also a problem of increase in the number of processes and deterioration of the productivity.

In response to this, in the producing process of composite resin molded product 10 in the present embodiment, melt-kneading (totally dry method) is performed together with coating resin 3, without performing the pretreatment by the wet dispersion for the purpose of defibrating natural fibers. In this method, without performing the wet dispersion treatment of natural fibers 2, it is possible to prevent the swelling of natural fibers 2 in the producing process and improve the water absorption rate of natural fibers 2 in composite resin molded product 10. By drying natural fibers 2 in advance or at the time of kneading, the water absorption rate in composite resin molded product 10 in the humid environments can be further improved. Since natural fibers 2 have the defibrated parts as described above, the fibers can have many contact points inside composite resin molded product 10, and the water absorption rate of composite resin molded product 10 can be increased through the contact points between the fibers.

In order to produce natural fibers 2 of the present embodiment by the totally dry method, it is preferable to apply a high shear stress at the time of kneading. Specific examples of the kneading tool include a single-screw kneader, a twin-screw kneader, a roll kneader, a Banbury mixer, and a combination thereof. A continuous twin-screw kneader and a continuous roll kneader are particularly preferable from the viewpoint of easy application of high shear and high mass productivity. A kneading tool other than the above may be used as long as the tool can apply a high shear stress.

(3) The composite resin composition of natural fibers 2 and coating resin 3 extruded from the melt-kneading device is crushed using a cutting machine or a crusher, thereby obtaining natural fibers 2 in which at least a part of the surface is coated with coating resin 3 in the present embodiment. Specific tools include pelletizers, ball mills, roll mills, hammer mills, wonder crushers, jet crushers and combinations thereof. A cutting or crushing tool other than the above may be used as long as the tool can maintain the state in which at least a part of natural fibers 2 is coated with coating resin 3.

(4) An injection-molded product as composite resin molded product 10 can be produced by dry-blending main agent resin 1 and natural fibers 2 coated with coating resin 3, kneading the fibers and the resin, and then injection-molding the product. The molding temperature at the time of injection molding is preferably 125% or less of the melting point of coating resin 3. When the molding temperature is higher than 125% of the melting point of coating resin 3, coating resin 3 melts and is dispersed in main agent resin 1 at the time of molding.

Hereinafter, examples and comparative examples in the experiments conducted by the inventors will be described.

(Example 1)

In Example 1, a cellulose composite poly(3-hydroxybutyrate-co-3-hydroxyvariate) (PHBV) resin molded product was produced by the following production method.

Coniferous pulp (trade name: NBKP Celgar, manufactured by Mitsubishi Paper Mills Limited) was used as a starting material for natural fibers. As a PHBV-degrading enzyme, PHB depolymerase extracted from a culture medium of a *Streptomyces* microorganism was used. The coniferous pulp and the PHB depolymerase were dry-blended to a mass ratio of 90:10 and ground by a roll mill to obtain an enzyme-supported cellulose filler.

Polylactic acid (trade name: TE-2000 manufactured by Unitika Ltd.) as a coating resin and the enzyme-supported cellulose filler were weighed and dry-blended so as to have a mass ratio of 50:50. After that, the product was melt-kneaded with a twin-screw kneader (KRC kneader manufactured by Kurimoto Iron Works). A screw of a medium shear type was used. The conditions for melt kneading were a material temperature of 200° C. and a rotation speed of 50 $min^{-1}$. The composite resin composition discharged from the twin-screw kneader was hot-cut to prepare cellulose composite polylactic acid resin pellets.

The produced cellulose composite polylactic acid pellets were crushed with a Wonder crusher (WC-3 manufactured by Osaka Chemical) to obtain cellulose fibers coated with a polylactic acid resin. The crushing condition was a rotation speed of 15000 rpm.

The cellulose fibers coated with the polylactic acid resin and PHBV (trade name: Y1000P manufactured by TianAn Biopolymer) as a main agent resin were weighed and dry-blended so as to have a mass ratio of 50:50. After that, the product was melt-kneaded with the twin-screw kneader (KRC kneader manufactured by Kurimoto Iron Works). A screw of a medium shear type was used. The conditions for melt kneading were a material temperature of 180° C. and a rotation speed of 50 $min^{-1}$. The composite resin composition discharged from the twin-screw kneader was hot-cut to prepare cellulose composite PHBV resin pellets having a mass ratio of the main agent resin, the enzyme-containing natural fibers, and the coating resin of 50:25:25.

After that, a test piece of a cellulose composite PHBV resin molded product was produced by an injection molding machine (180AD manufactured by Japan Steel Works, Ltd.). The conditions for producing the test piece include a temperature of the main agent resin of 200° C., a metal die temperature of 50° C., an injection speed of 100 mm/s, and a holding pressure of 100 Pa. The shape of the test piece was changed according to the evaluation items described below.

(Evaluation of Water Absorption of Fiber)

The water absorption of the fiber was evaluated by measuring the moisture percentage of the fiber by the method specified in ASTM D1909. Specifically, the weight of the fiber dried at 80° C. for 24 hours was measured, and was used as the reference weight. Then, the weight of the fiber maintained at a temperature of 20° C. and a humidity of 65% for 24 hours was measured. The moisture percentage was calculated by taking the weight increase from the reference weight as water. Those having a moisture percentage of less than 5% were evaluated as "C", and those having a water content of 5% or more were evaluated as "B". The moisture percentage of the coniferous pulp was 6.5%, and the evaluation was "B".

(Fiber End Part Defibration)

The obtained cellulose composite PHBV resin molded product was immersed in a chloroform solvent to dissolve the PHBV and the polylactic acid, and the shape of the remaining cellulose fibers was observed by SEM. The end parts of the fibers were in a defibrated state.

(Evaluation of Elastic Modulus of Composite Resin Molded Product)

A three-point bending test was carried out using the obtained test piece having a dumbbell-shape of a JIS K7139 type A12 size. Here, as a method for evaluating the elastic modulus, those having a numerical value of less than 200 MPa were evaluated as "C", and those having a modulus of 200 MPa or more were evaluated as "B". The elastic modulus of the test piece was 259 MPa, and the evaluation was "B".

(Deterioration Test of Composite Resin Molded Product)

A deterioration test was carried out using the obtained test piece having a dumbbell-shape of the JIS K7139 type A12 size. The test piece was held at a temperature of 60° C. and a humidity of 40% for 48 hours. An environment of 60° C. is an accelerated test of about 50 times that in a normal atmosphere at room temperature. A three-point bending test was carried out using the test pieces after the deterioration test. As a deterioration evaluation method, those having a decrease rate of the elastic modulus less than 10% with respect to the elastic modulus before the acceleration test were evaluated as "B", and those having a decrease rate of elastic modulus of 10% or more were evaluated as "C". The decrease rate of the elastic modulus of the test piece was 5%, and the evaluation was "B".

(Evaluation of Biodegradability of Composite Resin Molded Product)

A biodegradation test was carried out using a test piece of bar shape made of the obtained cellulose composite resin molded product. 50 g of a compost planting source (YK-11, manufactured by Yawata Bussan Co., Ltd) was put into a plastic container. A test piece of bar shape having a height of 20 mm, a width of 10 mm, and a thickness of 3 mm, whose weight was measured in advance, was embedded in this planting source, and kept at a temperature of 58° C. and a humidity of 50%. The weight loss thereof after 2 months was evaluated. As a method for evaluating the biodegradation rate, a weight loss value of 50% or more was evaluated as "A", a weight loss value of 40% or more and less than 50% was evaluated as "B", and a weight loss value of less than 40% was evaluated as "C". The biodegradation rate of the test piece was 42%, and the evaluation was "B".

(Example 2)

In Example 2, a cellulose composite PHBV resin molded product was produced with the mass ratio of the main agent resin, the enzyme-containing natural fiber, and the coating resin changed to 67.5:25:7.5, and with other material conditions and process conditions being the same as in Example 1. As for the evaluation, the same evaluation as in Example 1 was carried out.

(Comparative Example 1)

In Comparative Example 1, an uncoated enzyme-supported cellulose filler was used. A cellulose composite PHBV resin molded product was produced with the mass ratio of the main agent resin and the enzyme-supported cellulose filler changed to 25:75, and with other material conditions and process conditions being the same as in Example 1. As for the evaluation, the same evaluation as in Example 1 was carried out.

(Comparative Example 2)

In Comparative Example 2, the polylactic acid resin as the coating resin and the enzymes were melt-kneaded at a mass ratio of 95:5 without using the natural fibers. A PHBV composite resin molded product was produced with the mass ratio of the main agent resin and the enzyme-containing polylactic acid resin changed to 50:50, and with other material conditions and process conditions being the same as in Example 1. As for the evaluation, the same evaluation as in Example 1 was carried out.

(Comparative Example 3)

In Comparative Example 3, an enzyme-supported PET fiber was produced by using a PET fiber having a fiber diameter of 20 μm and a fiber length of 100 μm instead of coniferous pulp. A PHBV composite resin molded product was produced with other material conditions and process conditions being the same as in Example 1. As for the evaluation, the same evaluation as in Example 1 was carried out.

(Comparative Example 4)

In Comparative Example 4, a polylactic acid composite resin molded product was produced using a polylactic acid resin instead of the PHBV resin as the main agent resin, with other process conditions being the same as in Example 1. As for the evaluation, the same evaluation as in Example 1 was carried out.

(Comparative Example 5)

In Comparative Example 5, a PHBV resin molded product was produced by using a PHBV resin as a raw material without using the natural fibers, the coating resin, or the enzymes, and with process conditions being the same as in Example 1. As for the evaluation, the same evaluation as in Example 1 was carried out.

FIG. 5 illustrates the configurations and measurement results of the composite resin molded products in Examples 1 and 2 and Comparative Examples 1 to 5.

As is clear from FIG. 5, in Examples 1 and 2 in which the enzymes supported on the natural fiber was protected by the coating resin, the elastic modulus was as high as 200 MPa or more, and the deterioration of rigidity was reduced as compared with Comparative Example 2 in a low humidity environment of 40% humidity. The biodegradation speed was accelerated as compared with Comparative Example 5. In the biodegradation evaluation, the biodegradation speed of Example 2, which has a smaller proportion of the coating resin, was higher than the biodegradation speed of Example 1.

As described above, it is confirmed that a composite resin having high elastic modulus, high durability and high biodegradability can be obtained by compositing the natural fibers supporting the enzymes on the surface, coating at least a part of the surface of the natural fibers with the hydrolyzable resin, and exposing the fibers on the surface of the composite resin molded product to increase the water absorption rate of the natural fibers is high.

Comparative Example 1, which was produced without using the coating resin, had an improved elastic modulus as compared with Comparative Example 5 due to the composite of the natural fibers, but the enzymes were not protected by the coating resin at the time of molding and the heat damage of the enzymes at the time of kneading and molding was large. Therefore, the biodegradation speed was lower than the biodegradation speed of Comparative Example 3, and the evaluation was "C".

In Comparative Example 2, which was produced without using the natural fibers, the elastic modulus was improved by the composite of the polylactic acid resin, but water was not absorbed into the composite resin molded product by the natural fibers. Therefore, the hydrolysis of the polylactic acid resin did not proceed, the biodegradation speed was lower than the biodegradation speed of Comparative Example 5, and the evaluation was "C".

In Comparative Example 3, which was produced by using the PET fibers instead of the coniferous pulp, the PET fibers had a low moisture percentage and had no water absorption. Therefore, in the biodegradability evaluation, the hydrolysis of the polylactic acid resin did not proceed, the biodegradation speed was lower than the biodegradation speed of Comparative Example 5, and the evaluation was "C".

In Comparative Example 4, which was produced by using the polylactic acid resin instead of the PHBV resin as the main agent resin, hydrolysis of the main agent resin proceeded in the deterioration test, the elastic modulus decreased, and the evaluation was "C". In the biodegradability evaluation, since the polylactic acid resin as the main agent resin has a lower biodegradation speed than the PHBV resin, the biodegradation rate also decreases and the evaluation is "C".

From the above-described evaluation, it is confirmed that a composite resin molded product having high elastic modulus, high durability and high biodegradability can be obtained by using natural fibers having water absorption and the biodegradable plastics, supporting the enzymes on the surfaces of the natural fibers, coating at least a part of the surface of the fibers with the hydrolyzable coating resin, and exposing the fibers on the surface of the composite resin molded product.

Appropriate combinations of any of the embodiment and/or examples among the various embodiment and/or examples described above are within the scope of the present disclosure, and effects of the respective embodiment and/or examples can be achieved.

INDUSTRIAL APPLICABILITY

According to the composite resin molded product according to the invention, it is possible to provide a composite resin molded product capable of controlling the mechanical strength and the biodegradation speed as compared to the biodegradable plastics in the related art. According to the invention, the characteristics of the main agent resin can be improved, and thus the composite resin molded product can be used as a substitute for general-purpose plastics derived from petroleum. Thus, the environmental load of various industrial products or daily necessities made of the general-purpose plastics derived from petroleum can be significantly reduced. Furthermore, the composite resin molded product can be used as packaging materials, daily necessities, home appliance housings, building materials, and the like.

What is claimed is:

1. A composite resin molded product, comprising:
a main agent resin; and
a plurality of natural fibers dispersed in the main agent resin,
wherein the plurality of natural fibers each contain a microorganism or an enzyme,
when the composite resin molded product is 100% by mass, a content rate of the plurality of natural fibers each containing the microorganism or the enzyme in the composite resin molded product is 10% by mass or more and 99% by mass or less, at least one of the plurality of natural fibers includes a defibrated part at an end part and an undefibrated central part in a fiber length direction, at least one of the plurality of natural fibers is exposed on a surface of the composite resin molded product, and at least a part of a surface of the at least one of the plurality of natural fibers is coated with a hydrolyzable coating resin.

2. The composite resin molded product of claim 1, wherein a moisture percentage in the plurality of natural fibers is 5% or more by a method specified in ASTM D 1909.

3. The composite resin molded product of claim 1, wherein the main agent resin in the composite resin molded product is a biodegradable resin containing any one selected from the group of polyhydroxyic acids, polyhydroxyalkanoates, poly (alkylene dicarboxylate) s, and modified starches.

4. The composite resin molded product of claim 1, wherein the hydrolysable coating resin has a melting point within a range equal to or higher than a melting point of the main agent resin and lower than a carbonization temperature of the plurality of natural fibers.

5. The composite resin molded product of claim 1, wherein the plurality of natural fibers each contain a fiber and the microorganism or enzyme supported on a surface of the fiber.

6. The composite resin molded product of claim 1, wherein the plurality of natural fibers are celluloses.

7. The composite resin molded product of claim 1, wherein at least one of the plurality of natural fibers has the undefibrated central part exposed on the surface of the composite resin molded product.

8. The composite resin molded product of claim 1, wherein the defibrated part at the end part is 5% or more and 50% or less of the fiber length of the entire natural fiber.

9. A production method for a composite resin molded product, comprising:

a step of preparing a microorganism or an enzyme, natural fibers, a hydrolyzable coating resin, and a main agent resin;

a step of including the microorganism or the enzyme in the natural fibers;

a coating resin melt-kneading step of melt-kneading the natural fibers containing the microorganism or the enzyme together with the coating resin, advancing defibration from an end part in a fiber length direction of each of the natural fibers containing the microorganism or the enzyme, and expanding a surface area of a defibrated part of the end part; and a step of molding the composite resin molded product after kneading coated natural fibers, obtained by coating at least a part of a surface of each of the natural fibers with the coating resin, together with the main agent resin.

10. The production method for a composite resin molded product of claim 9, wherein a molding temperature in the step of molding the composite resin molded product is set to a temperature of 125% or less of a melting point of the coating resin.

11. A composite resin molded product, comprising:

a main agent resin; and a plurality of natural fibers dispersed in the main agent resin, wherein the plurality of natural fibers each contain a microorganism or an enzyme, when the composite resin molded product is 100% by mass, a content rate of the plurality of natural fibers each containing the microorganism or the enzyme in the composite resin molded product is 10% by mass or more and 99% by mass or less, at least one of the plurality of natural fibers is exposed on a surface of the composite resin molded product, at least a part of a surface of the at least one of the plurality of natural fibers is coated with a hydrolyzable coating resin, and wherein the coating resin is a polyester resin.

12. The composite resin molded product of claim 11, wherein the coating resin is polylactic acid or polybutylene terephthalate.

* * * * *